United States Patent [19]

Salvado

[11] Patent Number: 4,897,796
[45] Date of Patent: * Jan. 30, 1990

[54] NONDESTRUCTIVE MEASUREMENT OF FRACTIONS OF PHASES IN MIXTURES AND COMPOSITE MATERIALS

[75] Inventor: Carlos A. Salvado, Carlsbad, Calif.

[73] Assignee: The Expert System Technologies, Inc., San Diego, Calif.

[21] Appl. No.: 275,072

[22] Filed: Nov. 22, 1988

[*] Notice: The portion of the term of this patent subsequent to Dec. 12, 2005, has been disclaimed.

Related U.S. Application Data

[63] Continuation of Ser. No. 930,122, Nov. 12, 1986, Pat. No. 4,794,545.

[51] Int. Cl.⁴ .................. G06F 15/46; G06F 15/20
[52] U.S. Cl. ........................... 364/497; 73/577; 73/599; 364/507
[58] Field of Search ............ 364/497, 499, 473, 507, 364/571.04, 571.07; 73/577, 597, 599, 622, 625, 628, 644, 661; 324/236; 250/390.04, 391

[56] References Cited

U.S. PATENT DOCUMENTS

| | | | |
|---|---|---|---|
| 3,019,637 | 2/1942 | Cook et al. | 73/628 |
| 4,165,649 | 8/1979 | Greer, Jr. | 364/507 |
| 4,259,868 | 4/1981 | Rao et al. | 73/597 |
| 4,361,154 | 11/1982 | Pratt | 73/597 |
| 4,462,082 | 7/1984 | Thiele et al. | 364/507 |
| 4,479,387 | 10/1984 | Wagner et al. | 73/622 |
| 4,494,408 | 1/1985 | DeLacy | 73/599 |
| 4,494,410 | 1/1985 | Van Bochove et al. | 73/644 |
| 4,499,770 | 2/1985 | Kriz | 73/599 |
| 4,507,967 | 4/1985 | Schlierelmann | 73/625 |
| 4,519,245 | 5/1985 | Evans | 73/579 |
| 4,575,634 | 3/1986 | Redler et al. | 250/390.04 |
| 4,639,669 | 1/1987 | Howard et al. | 73/597 |
| 4,745,809 | 5/1988 | Collins et al. | 73/661 |
| 4,763,071 | 8/1988 | McGee et al. | 324/236 |
| 4,794,545 | 12/1988 | Salvado | 364/497 |

OTHER PUBLICATIONS

ASTM Standard C613-67 "Standard Test Method for Resin Content of Carbon and Graphite Prepregs by Solvent Extraction" Amer. Soc. Testing Materials, 1985.

Williams et al. "Ultrasonic Attenuation as an Indicator of Fatigue Life of Graphite Fiber Epoxy Composite", Materials Evaluation, May 1980, pp. 33-37.

Primary Examiner—Parshotam S. Lall
Assistant Examiner—Kevin J. Teska
Attorney, Agent, or Firm—Gregory O. Garmong

[57] ABSTRACT

The weight fractions of the phases of a composite material working specimen are determined nondestructively by first performing a sufficient number of nondestructive and destructive calibration measurements on the properties of calibration specimens. The information learned from the calibration specimens is used in combination with nondestructive measurements of the working specimen to determine the fractions of the phases therein, without damaging the working specimen. In one version of this approach, ultrasonic measurements are used to determine fractions of the fiber and matrix in a nonmetallic composite material.

20 Claims, 1 Drawing Sheet

NONDESTRUCTIVE MEASUREMENT OF FRACTIONS OF PHASES IN MIXTURES AND COMPOSITE MATERIALS

This is a continuation of application Ser. No. 06/930,122, filed Nov. 12, 1986, now U.S. Pat. No. 4,794,545.

BACKGROUND OF THE INVENTION

This invention relates to testing techniques for mixtures and composite materials, and, more specifically, to a process for measuring nondestructively the fractions of the phases of working specimens.

Many of the materials used in modern technology, particularly those used for their structural properties, are mixtures of several phases which generally retain their inherent character within the mixture. One important class of such mixtures is composite materials, wherein at least two distinct phases are bonded together to form a single material. In a typical structural composite material used in aerospace applications, oriented, high-strength, low ductility graphite, carbon, Kevlar TM or glass reinforcement fibers are embedded in a resin matrix which binds and protects the fibers. The properties of the resulting composite material reflect the high strength and elastic properties of the reinforcement fibers, yet the composite material is formable and usable in a variety of applications.

One of the most important parameters characterizing such a composite material is the weight (or, equivalently, the volume) fractions of the phases. That is, such a composite material can be described as containing a particular weight fraction of a first phase, another particular weight fraction of a second phase, and so forth, so that the weight fractions of all the phases total 1.0. The greater the amount of a particular phase present in the composite material, the greater, is its influence on the overall or total composite material properties.

For many properties such as elastic modulus, the total composite property is the linear sum of the same property for each phase times the volume fraction of that phase present, summed over all of the phases making up the composite material. This relationship is called the rule of mixtures, and is obeyed exactly for some properties and nearly exactly for many other properties. In any event, the functional relationship between the properties of individual phases and the total composite property is important in systematic design work using composite materials. One of the attractive features of composite materials is that they may be tailored to exhibit specific required properties by varying the fractions and arrangement of the phases. The relationship between the properties of individual phases and the total composite property has been the focus of much scientific and engineering attention.

Once a composite material has been designed to have a particular combination of properties, it must be manufactured to the design specifications and inspected to be certain that the manufacturing process actually resulted in the desired material. After manufacture and during service, the composite material must be inspected periodically to ensure that its properties have not changed during use. For example, absorption of moisture by the nonmetallic matrix, due to environmental exposure, can seriously degrade the composite properties. In both types of inspection procedures, measurement of the weight fractions of the phases is necessary because the properties of the composite material depend directly upon the weight or volume fractions of the phases, in the manner previously discussed.

The measurement of the weight fractions of the phases in the final composite material is not easy to perform, because portions of the phases are buried inside the composite material and are not readily visible to the naked eye nor measurable by external instruments. The most common approach to the measurement of the fractions of the phases during manufacturing is to section random samples of the material so that the internal structure can be inspected and the volume fraction determined (which then can be converted to a weight fraction, if desired), or to remove the matrix phase and weigh the amount of the fiber reinforcement phase to calculate a weight fraction (which then can be converted to a volume fraction, if desired, with knowledge of the densities of all of the phases of the composite material and the density of the composite material itself). In either event, the specimen that is investigated is destroyed and cannot be reused. A destructive testing program of this type usually requires a cost expenditure of about $40 to $150 per specimen examined, which cost tends to reduce the number of specimens tested and the reliability of the testing program. The testing procedure requires about ½ to about 3 hours, preventing real time control of the manufacturing process based upon the measurements.

Service determinations of weight or volume fraction are even more difficult, since the composite material is usually bonded into a structure which cannot be sectioned or dissolved. The composite material will also have been subjected to various changes during its service lifetime, which may influence its properties. One cannot therefore assume that the composite material in service has phase fractions and phase properties within acceptable limits, simply because the original material was acceptable. As an example, many resin matrix materials absorb moisture during service, changing the effective phase weight fractions of the matrix and the fibers, with respect to the weight of the composite, and the physical properties of the matrix. Because of this possibility, it is necessary to determine the phase fractions and sometimes the properties during service, to be certain that the composite material properties remain within the design limits.

Various types of measurement techniques have been developed to gain information about the internal structure of mixtures and composite materials, including the destructive techniques described above. However, all suffer from the shortcoming that quick, accurate, and inexpensive measurements of the phase fractions of working specimens cannot be made in a nondestructive fashion. Accordingly, there exists a need for a new technique for measuring the weight or volume fractions of the phases of a mixture, such as composite materials and the many other types of mixtures whose structures must be understood and characterized. The present invention fulfills this need, and further provides related advantages.

SUMMARY OF THE INVENTION

The present invention provides a process for determining the weight or volume fractions of the phases in a working specimen mixture, such as a composite material, in a rapid, nondestructive manner. The approach utilizes actual calibration data gained from measurements of mixtures of the same type as the working specimen, to maximize the accuracy of the measurements and to minimize the errors that might result from a purely theoretical treatment wherein there could be a deviation from theory for particular specimens. The method is generally applicable to mixtures and composites of an arbitrary number of phases, with those mixtures having more phases requiring that more information be known or gained from measurements of calibration specimens. The approach is readily applied both to repetitive nondestructive measurements of large numbers of specimens in a factory fabrication inspection procedure, and also to field measurements of working specimens in service or mixtures found in the field.

In accordance with the invention, a process for performing a nondestructive determination of the weight fractions of the phases present in a working specimen of a mixture, comprises the steps of selecting a series of nondestructively measurable properties of the phases of the mixture, each of which properties vary with the weight fractions of the individual phases in a known way and are summed over the phases to define a total mixture value for that property, thereby forming a system of simultaneous equations for the mixture properties as a function of the sum of products of a coefficient of variation times the weight fraction of each phase; measuring each of the measurable mixture properties on a sufficient number of calibration specimens having different weight fractions of the phases, and then destructively determining the weight fractions of the phases for the calibration specimens, thereby determining the coefficients of variation of the system of equations; and nondestructively measuring each of the measurable mixture properties on the working specimen of unknown weight fractions, and solving the system of equations for the weight fractions of the phases present in the working specimen. Equivalently, the same procedure may be performed using volume fractions rather than weight fractions, if that approach is more convenient in the circumstances, because the weight fractions are related to the volume fractions in a known, single-valued way through the densities of the phases and the composite material.

As used herein, a mixture is a heterogeneous mechanical blend of two or more phases which retain their physical identities in the mixture. In such a mixture, the phases are identifiable on a macro scale. In a mixture, as that term is used here, there may or may not be bonding between the phases. Where bonding occurs, the mixture is termed a composite material. While under some definitions of the term "mixture" a composite material would not be a mixture because the phases are bonded, it is intended that the term not be so narrowly interpreted here. As used herein, a composite material is one type of mixture.

Scientific studies have been performed to determine that certain measurable, single valued properties of a mixture such as a composite material can be described as a sum over all the phases, of a coefficient of variation of the property for each phase times the volume fraction of the phase in the mixture. Sometimes the coefficient of variation is simply the property in question in the phase, when measured apart from the composite. In other cases, however, the variation is more complete, either functionally or because the property of a phase differs when it is incorporated into the mixture or composite material (its "in-situ" behavior), as compared with its behavior apart from the composite material (its "bulk" behavior).

It will be appreciated that for some mixtures the properties of some phases will be known from prior experience, because the in-situ property is the same as its bulk property, and because the functional variation is known from prior studies. The in-situ properties of other phases may not be known, because the in-situ behavior is different from the bulk behavior. As an example, in a two-phase composite of carbon fiber reinforcements in a resin matrix, the elastic properties of the fiber reinforcements in-situ are essentially the same as those of the carbon fibers in bulk. The contribution of the elastic properties of the resin matrix to composite elastic properties is less predictable, since the contribution is influenced by processing parameters, environment, and chemical composition. In performing the process of the invention, it is therefore usually acceptable and convenient, but not necessary, to use the previously known fiber reinforcement properties and functional variation, but it may be necessary to determine the in situ resin matrix properties from the calibration specimen. In the general case, the more properties that are known from prior experience to the predictable within the composite material, the fewer actual measurements that must be performed on calibration specimens to determine the remaining variation.

The coefficients of variation that must be determined from measurements of calibration specimens are determined by measuring the mixture properties of interest for the calibration specimens, using specimens that are expendable and may be destroyed. Only a few such specimens are required to obtain calibration data enabling nondestructive testing of thousands of working specimens. The fractions of the phases are measured by destroying each of the calibration specimens by sectioning, chemical attack, thermal attack, or the like, and directly measuring the weight or volume fractions. In combination, the coefficients of variation known from prior experience, the measured mixture properties for the calibration specimens, and the measured phase fractions for the calibration specimens, permit the calculation of all of the coefficients of variation for the measurable properties of interest.

The number of calibration specimens that must be measured depends upon the extent of prior knowledge of the coefficients of variation of the j properties of interest. Generally, for a mixture with n phases, nondestructive calibration measurements of j properties each are performed on a series of n calibration specimens, and n destructive measurements of the weight fractions of the phases are performed on those calibration specimens. When j is equal to n, the system is determined, and when j is greater than n, the system is overdetermined. The system must be determined or overdetermined to permit the coefficients to be calculated, or otherwise additional information is required. When the system is overdetermined, the solutions appear in a least squares sense.

However, the number of required measurements of calibration specimens may be reduced if there is prior information about the coefficients. If r is the number of properties whose coefficients of variation are known for all of the n phases of the mixture, then only (n−r) calibration specimens must be measured to permit calculation of the remaining coefficients of variation.

It will be appreciated that the number of calibration specimens referred to herein as being required is a minimum value. Typically, more calibration specimens will be measured for statistical certainty and to reduce variations introduced through random variation or through measurement error.

Once the coefficients of variation are known, the fractions of the phases for a working specimen are determined by measuring the values of the properties of interest for that specimen, and solving the simultaneous equations for the unknown phase fractions.

It is not necessary to destroy the working specimen, as the measurable properties are selected to be measurable without damaging the working specimen. The difference between the calibration specimens and the working specimens must be kept in mind. The calibration specimens are a few specimens of the same type as the working specimen, but which are expendable. It is not necessary to destroy the calibration specimens to be able to measure the measurable properties, as these properties are selected because they can be measured nondestructively on the working specimens. The calibration specimens are destroyed only to measure the fractions of the phases to solve for the unknown coefficients of variation. Once these coefficients are known for that type of mixture, then it is not necessary to destroy the working specimen when the measurable properties are determined, assuming that the coefficients of variation as measured for the calibration specimens do not vary when measured for the working specimens.

This validity of this assumption of unchanging coefficients of variation can be ensured by selecting properties where the coefficients do not have strong variation with phase fractions, and by selecting calibration specimens that are generally within the range of expected property variations for the working specimens. The selection of calibration specimens with phase fractions close to those of the working specimens is usually not difficult, as in most cases the composite materials are manufactured to a standard, and there are usually relatively minor deviations from the standard. The calibration specimens are selected from the usual range of deviations, and the calculated coefficients of variation therefore reflect the normal range of deivation from the standard.

The values of the coefficients of variation, once determined from the measurements of the calibration specimens, can be repeatedly used in measurements of the fractions of the phases in an indefinitely large number of working specimens. In one approach, the coefficients of variation are carefully determined in a controlled environment for the calibration specimens of the mixture of interest. A number of calibration specimens may be studied to determine the coefficients in a least squares sense, minimizing error that may arise because of experimental error and statistical variation. The equations describing the variation of mixture properties, with the determined coefficients of variation, are programmed into a microcomputer. The measurements of the phase fractions of a series of working specimens are then performed automatically or semi-automatically by tests selected for adaptation to this automated approach. Calculations of the phase fractions for each working specimen are made by supplying the working specimen test data to the microcomputer, wherein the calculations of the phase fractions are performed no more than a few seconds after completion of the measurements.

The present approach is further illustrated by an exemplary embodiment involving the determination of the fractions of the phases in a composite material having a fiber of known properties and coefficient of variation, a matrix whose coefficient of variation may vary when the matrix is incorporated into the composite material, and wherein volume is conserved. Such a situation may arise in practice because the elastic properties of the fiber do not change when the fiber is incorporated into the matrix, but the elastic properties of the matrix may vary due to a stress state, uneven curing, unexpected chemical reactions, or the like. In such an approach, a process for performing a nondestructive determination of the weight fractions of the phases of a composite material working specimen having as phases an elastic fiber and a resin matrix, wherein the slowness of an ultrasonic wave propagated through the fiber is known, and wherein the in-situ slowness of an ultrasonic wave propagated through the matrix may differ from that measured when the matrix material is not incorporated into the working specimen, comprises the steps of determining the in-situ slowness of an ultrasonic wave propagating through the matrix, by the steps of measuring the slowness of an ultrasonic wave in a composite calibration specimen, destructively determining the volume fractions of the fiber and matrix for the calibration specimen, and calculating the in-situ slowness of an ultrasonic wave in the matrix as the reciprocal of the volume fraction of the matrix, times the difference between the slowness of an ultrasonic wave in the working specimen less the product of the slowness of an ultrasonic wave in the fiber times the volume fraction of the fiber, all determined for the calibration specimen; measuring the slowness of an ultrasonic wave in the working specimen, which is not destroyed in the measurement; and calculating the volume fraction of the matrix in the working specimen as the slowness of the ultrasonic wave in the working specimen, less the known slowness of the ultrasonic wave in the fiber, divided by the difference between the slowness of the ultrasonic wave in the matrix, as determined from the calibration specimen, less the known slowness of the ultrasonic wave in the fiber.

Variations of this embodiment are used when the coefficients of variation of both the matrix and the fibers are known, and where both are unknown. In the first case, where both coefficients of variation are known from prior experience, no measurements of any calibration specimens are required. The volume fraction of the matrix is determined by a single measurement of the ultrasonic slowness of the working specimen. In the second case, where neither coefficient of variation is known, two calibration specimens of differing phase fractions must be measured to determine the coefficients of variation, and these values are then used in conjunction with measurements of the working specimens.

The measurements of composite properties of both the calibration and working specimens are preferably made by an ultrasonic technique, which is readily adapted to rapid, automated, nondestructive testing of numbers of specimens. The ultrasonic test measures "slowness" of an ultrasonic wave in the specimens, which is the reciprocal of velocity. It has been established that the composite slowness is the sum of the slowness in each phase times the volume fraction of the phase, and is not affected significantly by the degree of bonding at interfaces between the phases.

In many composite materials, the fiber reinforcement phase is elastic, and its slowness ordinarily does not vary due to the incorporation of the fiber into the composite material. That is, the slowness of the ultrasonic wave in the in-situ fiber reinforcement is the same as in the bulk fiber. Available known data for the slowness in the bulk fiber is therefore used in the calculation.

On the other hand, the slowness of the ultrasonic wave in the resin matrix may or may not be the same as in the bulk material. If it is known to be the same, then no measurements of calibration specimens are required. If it is known not to be the same, or if there is doubt, then measurements of a calibration specimen are used to determine the coefficient of variation of slowness in the matrix.

The process of the preferred approach can be accomplished using automated test apparatus for sequentially testing series of working specimens, once the calibration test have been performed. As an example, the process can be arranged to test large numbers of prepreg specimens for volume fraction as the prepreg is manufactured. Each test is performed in a time of on the order of 1 second, and a running record and fabrication evaluation can be maintained. That is, the fractions of the phases can be evaluated nearly continuously just after the product is manufactured, and manufacturing process adjustments can be made to correct deviations discovered by the preferred process. This type of feedback control has not heretofore been possible.

The present process finds immediate application in evaluation of composite materials, an important class of mixtures. However, the process also finds important applications in other areas where mixtures must be evaluated, such as blending control of aggregates used in concrete manufacture, determination of the amount of reinforcement wire in automobile tires, determination of mineral fractions in ores, and the like, to name a few.

The process in its general form is highly flexible and adaptable to measuring many different types of materials. Ultrasonic measurements are only one technique that may be used in the evaluations. Light, electrical, magnetic, electromagnetic, and other forms of waves and radiation may likewise be used as properties to determine the weight and volume fractions of the phases, once the functional dependence of the composite property on phase fraction is known.

It will now be appreciated that the present invention provides an important advance in the field of nondestructive testing of mixtures, including composite materials. Once the functional dependence of a particular property with phase fraction is known, the coefficients of variation can be determined from either known information or by testing a sufficient number of calibration specimens. With proper selection of the properties to be measured, the process is readily adapted to automated testing of working specimens. Other features and advantages of the invention will be apparent from the following more detailed description, taken in conjunction with the accompanying drawings, which description illustrates, by way of example, the principles of the invention.

DETAILED DESCRIPTION OF THE PREFERRED EMBODIMENT

Figure 1:
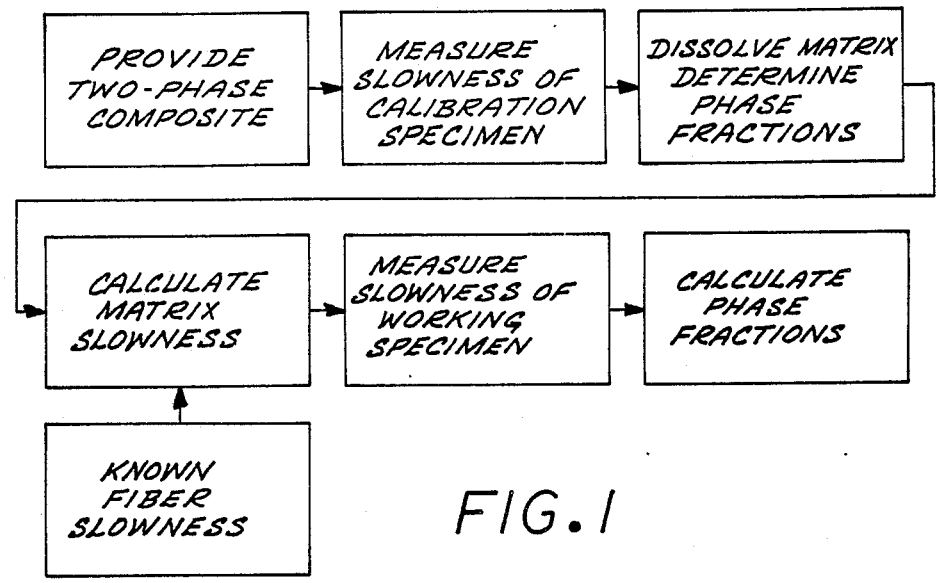
FIG. 1 is a process flow chart for a preferred embodiment of the invention.

The preferred embodiment is one case of the more general approach of the invention, and it is helpful to outline the general approach before proceeding to the preferred embodiment. Many physical properties of a mixture depend upon the nature and volume fraction of the phases making up the mixture. In general terms, $$C_m = \text{sum} (C_1 \times fu(P_i)),$$

where $C_m$ is the mixture property of interest, $fu$ indicates a general functional variation, $P$ is the volume fraction of a phase expressed in the appropriate physical terms, $C_1$ is the coefficient of variation, and the summation is made over the n total phases of the mixture. Even if the coefficients of variation $C_i$ are known, a single measurement of a composite property is not sufficient to calculate the unknown phase fractions $P$, for n greater than unity.

However, if a series of j equations of the above general form is written for j measurable properties or characteristics of the mixture, then it is possible to determine the phase fractions $P$ by first finding the values of $C_i$ from known information or from measurements of calibration specimens, and then measuring the j properties for a single working specimen:

$$C_{1m} = \text{sum} (C_{1i} \times fu(P_i))$$

$$C_{2m} = \text{sum} (C_{2i} \times fu(P_i))$$

$$C_{jm} = \text{sum} (C_{ji} \times fu(P_i))$$

The value of j must be at least as great as n for a solution of the equations. If j is equal to n, the system of equations is said to be determined. If j is greater than n, the system of equations is said to be overdetermined, there is redundance in the solution, and a solution in a least squares sense is possible. If j is less than n, more information is required to reach a unique solution.

The above set of equations is sufficient for a solution, but it is desirable that for simplicity in solution the equations be linear in P, so that $$fu(P_i) = P_i.$$

It is also desirable that the properties P be readily determined in measurements of specimens, and not be affected significantly by interfaces within the mixture, inasmuch as the present invention is used to determine volume fractions, not interfacial characteristics.

In addition to measurable properties, according to the principle of conservation of mass, the sum of the weight fractions is unity:

$$1 = \text{sum} (P_{i,w})$$

where w denotes a weight fraction.

The coefficients of variation $C_i$ are determined in one of two ways. For some phases, $C_i$ for the in-situ phase is the same as the property measured in bulk, and the selection of measurable properties is made with this consideration in mind. This is the case for most hard, strong, elastic fiber reinforcement materials used in composite materials. If the in-situ values of $C_i$ are the same as the bulk properties for all of the properties required, then the coefficients are determined and there is no need to do testing of calibration specimens.

For many phases of interest and measurable properties, however, the value of $C_i$ is not necessarily identical to the comparable bulk property. One important practical example is the resin matrix of a fiber reinforcement/resin matrix composite material. The resin matrix may absorb moisture or be in an unknown state of cure when present as the matrix of the composite, and in certain cases it is not possible to assume that the in-situ property is identical to the comparable bulk property.

In such cases, the coefficient of variation for the property is determined by measuring a number of calibration specimens sufficient for the determination. Where there are n phases whose phase fractions are eventually to be determined and r of the properties are such that all of the coefficients of variation of the phases are previously known or can be determined from the bulk data, then the number of calibration specimens that must be tested to determine the remaining coefficients of variation is (n−r). Each of the properties of interest for each of the calibration specimens is measured. The phase fraction of each of the phases of each of the calibration specimens is measured, typically by destructively sectioning or removing portions of the calibration specimens.

With this information derived from the calibration specimens, namely all of the composite properties, all of the phase fractions, and all of the known coefficients of variation, the above equations can be solved for the remaining unknown coefficients of variation. Where the equations are linear, the solution is readily accomplished by matrix techniques. A system of linear equations is preferred, and the properties to be measured are chosen with this consideration in mind. However, when this is not possible, nonlinear properties and equations may be used and the system of equations is solved with greater difficulty.

Once all of the coefficients of variation $C_i$ are known, including those which vary in an in-situ manner, the fractions of the phases of working specimens may be determined by measuring composite properties of the working specimens, and without destroying the working specimens. Each of the measurable composite properties is measured, and the equations (whose coefficients of variation were previously supplied or determined) are solved for volume or weight fractions of the phases. Once either the volume or weight fractions are known, the other can be calculated, according to the equation:

$$P_{i,v} = P_{i,w}(D_c/D_i)$$

wherein P is the fraction of the phase, D is density, i is the ith phase, v is by volume, w is by weight, and c refers to the composite.

In an application of these principles, the properties of a composite material having four phases is determined from the assumption of conservation of volume, and measurements of ultrasonic slowness S, which is the reciprocal of velocity of an ultrasonic wave, ultrasonic attenuation A, which is the reduction of amplitude of an ultrasonic wave, and density D, using the following linear equation, expressed in matrix form. Such a situation of the need to determine four phases can arise because the composite includes a matrix, a fiber, a moisture phase, and a paper separation material.

$$\begin{pmatrix} 1 & 1 & 1 & 1 \\ S_1 & S_2 & S_3 & S_4 \\ A_1 & A_2 & A_3 & A_4 \\ D_1 & D_2 & D_3 & D_4 \end{pmatrix} \begin{pmatrix} V_1 \\ V_2 \\ V_3 \\ V_4 \end{pmatrix} = \begin{pmatrix} 1 \\ S_m \\ A_m \\ D_m \end{pmatrix}$$

The leftmost matrix, a 4×4 matrix termed g, contains the coefficients of variation for the 4×1 volume fraction vector, termed M. The 4×1 composite properties vector, d, is the rightmost matrix of the equation. Because the coefficients of variation for one property, volume fraction, are known from the assumption of conservation of volume, there remain three properties whose coefficients of variation are not known. Therefore, the S, A, and D properties must be measured nondestructively for three calibration specimens, and the V values measured destructively for each of those specimens. The slowness properties S and the ultrasonic attenuation properties A are measured by ultrasonic wave propagation, and the density property D is measured by a liquid displacement technique, or be a more sophisticated technique such as gamma ray or beta ray emission. The equation can then be solved for all the remaining terms of g.

Once g is known, nondestructive measurements of the components of the d vector on a working specimen permits the equation to be solved for the M vector for the working specimen, by a direct matrix transformation:

$$M = (_gT_g) - 1_gT_d.$$

This matrix transformation is a general form applicable to a determined or overdetermined system, which can be simplified, for the usual case of a square n x n matrix, to $$M = g^{-1}d$$

In the presently preferred embodiment of the invention, the volume fractions of a working specimen of a two-phase composite material, having an elastic fiber reinforcement phase f and a resin matrix phase m, are evaluated. The determinations are based upon two experimental observations for such materials: that the sum of the volume fractions of the phases is unity (i.e., conservation of volume), and that the sum of the ultrasonic slowness of the fiber ($S_f$) times the volume fraction of fiber ($P_f$) plus the ultrasonic slowness of the matrix ($S_m$) times the volume fraction of the matrix ($P_m$) being the ultrasonic slowness of the composite material ($S_c$). The slowness of an ultrasonic wave in the composite is independent of, or at most very weakly dependent upon, the nature of the interfaces in the composite material. Slowness can be readily measured in a nondestructive manner on working specimens. These measurements may be performed by apparatus that operates in an automated manner.

There are three possible cases of interest in applying this approach to the testing of actual composite measurements. In the first case, the values of the coefficients of variation $S_f$ and $S_m$ are known for the in situ properties from measurements of bulk properties. This case is found for a number of practical composite materials of interest. No measurements of calibration specimens are required, and the volume fractions of the phases of the working specimen can be determined from a single measurement of the composite slowness of that specimen.

In the second case, the in situ properties of one phase (specifically, the matrix) are different from the bulk properties, and measurements of a calibration specimen are required. This case may arise because the matrix cures unevenly due to the proximity of the fibers, for example. The determinations required for this second case are illustrated in FIG. 1. The slowness of the ultrasonic wave in the fiber depends upon the elastic modulus and the density of the fiber, both of which do not change when the fiber is incorporated into the matrix. The in suit coefficient of variation of fiber slowness is therefore equal to the bulk slowness, which is often readily available for a particular fiber choice. Only one coefficient of variation, matrix slowness, must therefore be determined from measurements of a calibration specimen. The matrix slowness is determined by measuring the composite slowness of a calibration specimen. Preferably, the calibration specimen is chosen so that the volume fraction of the phases therein is about that of the working specimen to be subsequently measured, so that the stress and cure states of the two specimens are about the same. The calibration specimen is then sectioned and examined microscopically to determine the volume fractions of the phases. Alternatively, the matrix of the calibration specimen may be dissolved away, and the remaining fiber reinforcement material weighed and converted mathematically to a volume fraction of reinforcement. The volume fraction of matrix is unity minus the fiber volume fraction (assuming that volume is conserved). The coefficient of variation of the ultrasonic wave in the matrix is the reciprocal of the volume fraction of the matrix, times the difference between the slowness of the ultrasonic wave in the working specimen, less the product of the slowness of the ultrasonic wave in the fiber times the volume fraction of the fiber. With this calculation complete, all of the coefficients of variation are known.

Next, the slowness of the ultrasonic wave in the working specimen of the composite material is measured. Only a single measurement on the working specimen is required, and the working specimen is not destroyed or otherwise physically altered. The ultrasonic measurement requires on the order of about one second to perform, using apparatus to be described subsequently. The volume fraction of the matrix is then calculated as the measured slowness of the ultrasonic wave in the working specimen, less the known slowness of the ultrasonic wave in the fiber, this difference being divided by the difference between the slowness of the ultrasonic wave in the matrix, as determined from the calibration specimen, less the known slowness of the ultrasonic wave in the fiber reinforcement. The volume fraction of fiber reinforcement is unity minus the volume fraction of the matrix.

In the third case, neither the fiber nor the matrix coefficient of variation of slowness is known. Measurements of ultrasonic slowness must be performed on two calibration specimens, and those calibration specimens must be sectioned or must have the matrix removed to determine the phase fractions. Once this information is determined, the coefficients of variation for the calibration specimens 1 and 2 are found by solving the equation:

$$\begin{vmatrix} P_{m,1} & P_{f,1} \\ P_{m,2} & P_{f,2} \end{vmatrix} \begin{vmatrix} S_m \\ S_f \end{vmatrix} = \begin{vmatrix} S_{c,1} \\ S_{c,2} \end{vmatrix}$$

(To have a meaningful solution, the phase fractions of the two calibration specimens should be sufficiently different. Alternatively stated, the product of $P_{m,1}$ times $P_{f,2}$ should be different from the product of $P_{m,2}$ times $P_{f,1}$.) By solving this equation for the coefficients of variation $S_m$ and $S_f$, and then using these coefficients in conjunction with the measurement of composite slowness for a working specimen in the manner previously described, the volume fraction values of $P_m$ and $P_f$ for the working specimen are determined.

In this two-phase system, under the assumption that the volume fractions of the phases add to unity, only a single type of measurement is required for the determination of volume fraction of the phases. Ultrasonic slowness has been chosen as the preferred quantity to be determined, as it is defined by a linear function, is not affected significantly by interface characteristics, and can be measured quickly and accurately for both working specimens and calibration specimens.

If the assumption of conservation of volume is not applicable, then two types of measurements would be required. For example, any two of ultrasonic slowness, ultrasonic attenuation, and density could be used as the basis for the determination of the phase fractions. Other composite properties such as optical, electrical, magnetic, electromagnetic, or the like could also serve as the basis for this determination.

Figure 2:
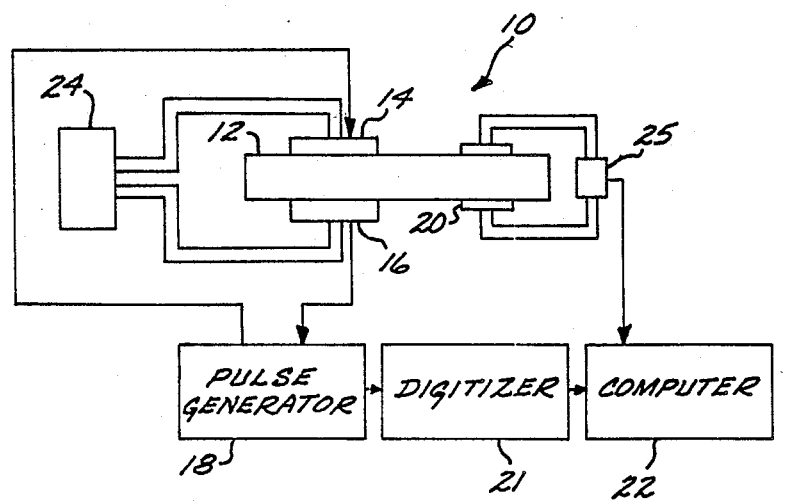
FIG. 2 is a side sectional view of an apparatus for practicing the invention.

Returning to the preferred embodiment wherein volume is conserved and a measurement of slowness is used, FIG. 2 illustrates an apparatus 10 for measuring composite slowness of specimens 12. The specimen 12 is contacted on one surface by a transmitter transducer 14, which transmits into the specimen 12 pulsed ultrasonic signals of proper frequency, such as from about $10^5$ to about $10^7$ Hertz. A receiver transducer 16 contacts the other side of the specimen 12 in a facing relation to the transmitter transducer 14, and receives the transmitted ultrasonic wave. A pulse generator 18 sends a pulsing signal to the transmitter transducer 14, and receives the transmitted signal from the receiver transducer 16. The waveform is digitized in a digitizer 21. The thickness or sonic path of the specimen is measured by a thickness gauge 20, and the thickness is provided to a minicomputer 22, along with the waveform and transit time from the digitizer 21. The slowness is the transit time divided by the thickness. This apparatus can be provided with a mechanism 24 upon which the transducers 14 and 16 are mounted, and a mechanism 25 upon which the thickness gauge 20 is mounted. The mechanisms 24 and 25 can open to permit a specimen 12 to be placed therein, closed for a measurement, and then open to allow extraction of the specimen 12 and insertion of a new specimen. The mechanisms 24 and 25 can be made to operate very rapidly, so that measurements of a series of working specimens can be accomplished rapidly, with each measurement requiring less than one second using automated apparatus.

The highly automated apparatus just described is particularly useful in performing production line measurements of composite materials as they are fabricated. For example, graphite fiber/resin matrix composites are typically fabricated as thin sheets of "prepreg", which is a loosely bound, uncured sheet about 0.004–0.008 inches thick and containing the fiber reinforcement and the matrix material, the matrix being in an uncured state. It is important to determine the weight fractions of the phases during production of the prepreg, since the prepreg is sold to a specification requiring particular weight fractions of the phases. In the art, the usual method of measuring the weight fractions of the phases on the production line has been to select working specimens on a periodic basis for destructive testing for weight fraction. The specimens were taken to a laboratory, where the matrix was dissolved away and the remaining fiber material weighed and converted to a volume fraction through calibration tables. Each such test costs about $40–$150 to perform, and requires about ½–3 hours to perform. The high cost reduces the number of specimens measured, and the time delay does not permit real time control of the fabrication process. The present invention, on the other hand, yields a weight fraction determination in only a few seconds, at a cost of less than $1 per test. Many tests can be performed and trends observed. If a trend from the desired weight fractions is observed, the manufacturing process can be adjusted accordingly.

The present approach can, of course, also be used in finished composites, before they are joined into structures, as a quality control check after the structure has been joined together, and even after the structure has been in service, as a check for deterioriation. In the latter application, it is not uncommon for one phase, particularly the resin matrix, to absorb moisture during service. The absorbed moisture causes deterioriation of composite properties. The present approach permits inspection of the weight fractions of the phases of a part in service. Such inspection is sufficiently accurate to identify the change in weight fraction of a phase due to absorbed moisture, and even the appearance of a new phase, containing bubbles of moisture.

The following example is presented to illustrate aspects of the invention, and should not be taken as limiting the scope of the invention in any way.

EXAMPLE

A commercial sheet of prepreg was obtained from the manufacturer. The sheet was composed of graphite fibers in an epoxy matrix, and had dimensions of about 12 inches by 12 inches by 0.005 inches thick. The sheet was cut into pieces 4 inches by 4 inches, and each of these pieces was cut into specimens 2 inches by 2 inches. The 2 inch by 2 inch samples from a 4 inch by 4 inch piece were stacked and evaluated by the process of the invention. They were then evaluated by the conventional procedure of dissolving the matrix and weighing the remaining fibers. Four such comparative tests were made, and the resin contents by weight of the samples are summarized in the following table:

| Sample No. | % Resin, Invention | % Resin, Conventional |
|---|---|---|
| 1 | 46.6 | 45.6 |
| 2 | 44.0 | 44.9 |
| 3 | 50.5 | 50.7 |
| 4 | 42.3 | 43.3 |

The resin contents as determined by the two approaches are reasonably consistent, with at most 1% difference between the two measurements. It is also apparent that the resin contents between areas of the piece of prepreg vary by several percent, even as measured by either of the two techniques. Consequently, it cannot be concluded that either of the techniques gives more accurate or more dependable result than the other. The prior art process has a number of sources of error, and the approach of the present invention may in fact be more accurate. However, the approach of the invention definitely yields the results more quickly and inexpensively than the conventional approach, and detects the variations between areas of several percent.

It will now be appreciated that the approach of the present invention can be used to determine volume fractions of multi-phase systems quickly and accurately. Calibration data is first obtained on a limited number of calibration specimens, and then this data is used in conjunction with test data to determine volume or weight fractions of the phases in working specimens. Although a particular embodiment of the invention has been described in detail for purposes of illustration, various modifications may be made without departing from the spirit and scope of the invention. Accordingly, the invention is not to be limited except as by the appended claims.

What is claimed is:

1. A process for determining fractions of phases present in a working specimen of a composite material, comprising the steps of:
   providing at least one calibration specimen of a composite material;
   nondestructively measuring a measurable property of the calibration specimen that varies with the fraction of the phases present in the calibration specimen;
   destructively measuring the fraction of the phases present in the calibration specimen;
   nondestructively measuring the measurable property of a working specimen; and
   determining the fractions of the phases present in the working specimen utilizing information obtained in the nondestructive measurement of the calibration specimen and the destructive measurement of the calibration specimen.

2. The process of claim 1, wherein only one calibration specimen is destructively measured.

3. The process of claim 1, wherein the working specimen is measured at a time of manufacture.

4. The process of claim 1, wherein the steps of nondestructively measuring are accomplished by an ultrasonic measurement technique.

5. The process of claim 1, wherein the steps of nondestructively measuring are accomplished by a technique that does not use ultrasonics.

6. The process of claim 1, wherein the working specimen is a prepreg composite material.

7. The process of claim 1, wherein the working specimen is a finished composite material.

8. The process of claim 1, wherein the composite material contains fibers, and the fibers are formed of a material selected from a group consisting of glass and carbon.

9. The process of claim 1, wherein the specimen being measured is mechanically deformed during each of the steps of nondestructively measuring.

10. The process of claim 1, wherein the first property is a property dependent upon elastic modulus.

11. The process of claim 1, wherein a thickness of the specimen is measured during each of the steps of nondestructively measuring.

12. The process of claim 1, wherein the steps of nondestructively measuring are accomplished by contacting a measuring device to a surface of the specimen being measured.

13. A process for determining fractions of phases present in a working specimen of a composite material, comprising the steps of:
   providing at least one calibration specimen of a composite material;
   nondestructively measuring a measurable property of the calibration specimen that varies with the fraction of the phases present in the calibration specimen, the step of nondestructively measuring including the substeps of elastically deforming the calibration specimen, and measuring the thickness of the calibration specimen;

determining the fraction of the phases present in the calibration specimen;

nondestructively measuring the measurable property of a working specimen, the step of nondestructively measuring including the substeps of elastically deforming the working specimen, and measuring the thickness of the working specimen; and determining the fractions of the phases present in the working specimen utilizing information obtained in the nondestructive measurement of the calibration specimen and the determination of the fractions of the phases present in the calibration specimen.

14. The process of claim 13, wherein the steps of nondestructively measuring the accomplished by an ultrasonic measurement technique.

15. The process of claim 13, wherein the steps of nondestructively measuring are accomplished by contacting a measuring device to a surface of the specimen being measured.

16. A process for determining a property of a working specimen of a composite material, comprising the steps of:

correlating a nondestructively obtained first property of a composite material to a second property of a composite material obtained utilizing at least one calibration specimen that is destroyed in obtaining the second property;

measuring in a nondestructive manner the first property on a working specimen of the composite material; and determining the second property of the working specimen from the nondestructively measured first property of the working specimen, and the correlation of the second property and the first property obtained from the calibration specimen.

17. The process of claim 16, wherein the first property is a property dependent upon elastic modulus.

18. The process of claim 16, wherein the second property is a fraction of a phase present in the composite material.

19. The process of claim 16, wherein a thickness of the working specimen is measured during the step of measuring.

20. A process for providing a calibration to be used in conjunction with a method for determining fractions of phases present in a working specimen of a composite material, comprising the steps of:

providing at least one calibration specimen of a composite material;

nondestructively measuring a measurable property of the calibration specimen that varies with the fractions of the phases present in the calibration specimen, the step of nondestructively measuring including the substeps of elastically deforming the calibration specimen by contacting a measuring device to a surface of the calibration specimen, and measuring the thickness of the calibration specimen;

determining the fraction of the phases present in the calibration specimen utilizing a procedure wherein the calibration specimen is destroyed and the fractions of the phases are measured; and correlating the nondestructively measured property and the fraction of the phases present determined destructively, in the calibration specimen, to form a calibration for measurements of a working specimen.

* * * * *